United States Patent [19]

Eichler et al.

[11] Patent Number: 4,604,470

[45] Date of Patent: Aug. 5, 1986

[54] PROCESS FOR THE ISOMERIZATION OF HALOGENATED THIOPHENES

[75] Inventors: Klaus Eichler, Eschborn; Ernst I. Leupold, Neu-Anspach, both of Fed. Rep. of Germany

[73] Assignee: Hoechst Aktiengesellschaft, Frankfurt am Main, Fed. Rep. of Germany

[21] Appl. No.: 737,179

[22] Filed: May 23, 1985

[30] Foreign Application Priority Data

May 25, 1984 [DE]  Fed. Rep. of Germany ....... 3419555

[51] Int. Cl.[4] ........................................... C07D 333/28
[52] U.S. Cl. ....................................... 549/81; 549/82
[58] Field of Search ................................... 549/81, 82

[56] References Cited

U.S. PATENT DOCUMENTS 2,492,622  12/1949  Coonradt ............................. 549/81

FOREIGN PATENT DOCUMENTS 1334243  10/1973  United Kingdom .

OTHER PUBLICATIONS

Chemical Abstracts, vol. 95(23), p. 574, No. 202731m, (Dec. 7, 1981).
Chemical Abstracts, vol. 69(11), p. 4092, No. 43711z, (Sep. 9, 1968).
Ullmann's Encyclopedia of Industrial Chemistry, 4th edition, vol. 23, p. 219.
S. Conde, Synthesis 1976, 6, p. 412.
Pentasil Family of High Silica Crystalline Materials–In Special Publication No. 33 of the Chemical Society, London, 1979.

*Primary Examiner*—Alan Siegel
*Attorney, Agent, or Firm*—Curtis, Morris & Safford

[57] ABSTRACT

The invention relates to a process for the isomerization of halogenated thiophenes on zeolite catalysts. In this manner, in particular, 2-chlorothiophene is isomerized to 3-chlorothiophene and 2-bromothiophene is isomerized to 3-bromothiophene. Particularly suitable zeolites are synthetic zeolites of the pentasil, mordenite or faujasite type in their acid form.

13 Claims, No Drawings

PROCESS FOR THE ISOMERIZATION OF HALOGENATED THIOPHENES

The present invention relates to a process for the isomerization of halogenated thiophenes.

Halogenated thiophenes are useful intermediates for the preparation of pharmaceuticals and plant protection agents (Ullmanns Enzyklopädie der technischen Chemie (Ullmann's Encyclopedia of Industrial Chemistry), 4th edition, volume 23, page 219). While 2-chlorothiophene can be synthesized by chlorination of thiophene, 3-chlorothiophene is not accessible via this route. Other synthesis routes are therefore required for its preparation, for example the reaction of 3-bromothiophene with CuCl (S. Conde, Synthesis 1976, 6, page 412). 3-Bromothiophene is prepared by dehalogenation of 2,3,5-tribromothiophene with zinc dust in acetic acid (Ullmanns Enzyklopädie der technischen Chemie (Ullmann's Encyclopedia of Industrial Chemistry), 4th edition, volume 23, page 219), while 2-bromothiophene can be obtained by bromination of thiophene in acetic acid by a simple route. All the methods known hitherto for the preparation of 3-chloro- or 3-bromo-thiophene either require very expensive starting substances or give only inadequate yields. Simple and inexpensive methods on an industrial scale have not hitherto been described.

It has now been found that halogenated thiophenes can be isomerized in good yields on zeolite catalysts.

The invention thus relates to a process for the isomerization of halogenated thiophenes, which comprises bringing a halogenated thiophene or a mixture of halogenated thiophenes into contact with a zeolite catalyst. The invention particularly relates to a process for the preparation of 3-chlorothiophene by isomerization of 2-chlorothiophene and a process for the preparation of 3-bromothiophene by isomerization of 2-bromothiophene on a zeolite catalyst. The term "halogenated thiophenes" is intended to include all thiophenes containing one to three halogen atoms, i.e., for example, in addition to chloro- and bromo-thiophene, also dibromo-, tribromo-, dichloro- and trichloro-thiophenes.

On the basis of the prior art, it was surprising and in no way predictable that halogenated thiophenes can be isomerized in such a simple manner with such high yields, as the examples show, and that 3-halogenothiophenes, which were hitherto difficult to prepare, can be prepared so easily from industrially accessible 2-halogenothiophenes.

To carry out the process according to the invention, a halogenated thiophene or a mixture of two or more halogenated thiophenes, either alone or together with one or more organic diluents, is brought into contact with the zeolite catalyst. Organic diluents which are in general used are benzene, an alkylbenzene, a monoor poly-halogenated benzene or a mixture of these. The molar ratio of the diluent to the halogenothiophene employed or the halogenothiophenes is in general 0:1 to 30:1, preferably 0:1 to 15:1.

Suitable zeolites are in general both naturally occurring and synthetic zeolites, preferably synthetic zeolites of the pentasil, mordenite or faujasite type, in particular synthetic zeolites of the pentasil type.

The definition of Kokotailo and Meier ("Pentasil family of high silicon crystalline materials" in Special Publication No. 33 of the Chemical Society, London, 1980) applies to the term pentasils. The pentasil family includes, for example, the synthetic zeolites ZSM-5 (U.S. Pat. No. 3,702,886), ZSM-8 (British Pat. No. 1,334,243), ZSM-11 (U.S. Pat. No. 3,709,979) and ZSM-23 (U.S. Pat. No. 4,076,842).

The Si/Al ratio of the pentasils is preferably 20 to 2000 and that of the mordenites is preferably 5 to 100. Pentasils or mordenites with a higher aluminum content can be adjusted here to the desired Si/Al ratio by removing some of the aluminum from the zeolite lattice by treatment with mineral acids, organic acids or chelating substances.

The zeolites are preferably employed in their acid form in the process according to the invention. These acid forms can be prepared by known methods from the alkali metal forms, such as are as a rule obtained in zeolite synthesis or occur as natural products, by complete or partial ion exchange. A usual method for the preparation of the H-form of a zeolite comprises, for example, initially converting the alkali metal form into the ammonium form by partial or complete ion exchange with an ammonium salt solution, and then converting this form into the H-form by calcining. However, the forms exchanged with alkali metal, alkaline earth metal or rare earth metal ions also exhibit catalytic activity.

The zeolite catalysts according to the invention in general consist of the catalytically active zeolite component and a binder material. The binder is necessary to bring the zeolite into an external form suitable for the process according to the invention.

Suitable binder materials are, above all, oxides or hydroxides of aluminum and the oxides or hydroxides of silicon, as well as layer silicates, for example of the kaolin or montmorillonite family.

This zeolite catalyst prepared in this way is usually first activated by calcination at temperatures between 300 and 700° C. before being used in the isomerization reaction according to the invention. For better stabilization of the catalyst, it is sometimes advantageous to carry out the calcining in the presence of steam, ammonia or mixtures thereof.

If the reaction is to be carried out in the gas phase, an advantageous simple procedure for carrying out the isomerization according to the invention comprises first introducing the halogenated thiophene or the halogenated thiophenes, if appropriate diluted as mentioned above, from a metering device into a vaporization zone and then passing the gas formed through an externally heated reaction tube filled with the catalyst. If the isomerization is carried out in the liquid phase, the thiophene or thiophenes, if appropriate diluted, are first warmed and then passed in liquid form through the reaction tube filled with the catalyst.

If appropriate, mixing with hydrogen, nitrogen and/or another carrier gas, hydrogen being preferred, is also effected in the vaporization or warming zone. It has proved advantageous here to heat up these gases to the reaction temperature before the mixing operation.

After leaving the reactor, the reaction products are cooled to remove the condensible contents. However, the isomerization according to the invention is not restricted to this procedure (fixed bed reactor), but can in principle also be carried out in other suitable types of reactor (for example fluidized bed reactor).

The throughput over the zeolite catalyst—expressed as the LHSV (Liquid Hourly Space Velocity, $h^{-1}$)—is in general between 0.05 and 10 $h^{-1}$, preferably between 0.2 and 5 $h^{-1}$.

The isomerization according to the invention is in general carried out at temperatures between 150 and 550° C., preferably at 180 to 350° C., and under pressures of 0.1 to 10 bar, preferably under normal pressure.

The isomer mixture formed can be separated by distillation by known processes. The unreacted starting substance can be recycled to the reactor.

If the activity of the catalyst slowly decreases due to coking, the catalyst can be regenerated from time to time. This is effected by passing oxygen, air, nitrogen/air, oxygen/air, oxygen/inert gas or air/inert gas over the deactivated catalyst at temperatures between 300 and 650° C. Nitrogen/air is preferred here. The temperature should not exceed 650° C. here at any point in the reactor. After regeneration, the catalyst again has the complete activity, as shown in Example 3.

The invention may be illustrated by the following examples, but these are in no way intended to be limiting.

EXAMPLES

Preparation of the catalyst 100 g of ZSM-5 powder in the Na-form (U.S. Pat. No. 3,702,886) were treated three times with 1 molar ammonium chloride solution at 100° C. for 5 hours, washed, dried and calcined in air at 550° C. for 5 hours. 65 g of the resulting powder were processed with 35 g of $Al_2O_3$ to extruded strands 1.6 mm in diameter, the strands were calcined at 500° C. for 4 hours and comminuted to a particle size of 0.25 to 1.0 mm and the material was calcined at 450° C. in a stream of nitrogen for 2 hours.

Description of the Apparatus 15 ml of the catalyst described above were introduced into a glass tube reactor with an internal diameter of 16 mm and a length of 50 cm and were covered with a layer of glass beads (for vaporization of the liquid reactants). The reactor was in an electrically heated oven. Liquid reactants were fed in via a metering pump and gases were fed in via a gas supply line, consisting of reducing valves and devices for measuring the pressure and flow rate. The condensible reaction products were condensed in a cold trap at 0° C. and analyzed by gas chromatography.

EXAMPLE 1

(Isomerization of 2-Chlorothiophene)

15 ml/hour of a mixture of 2-chlorothiophene and benzene in a ratio of 1:10 were passed with 5 l/hour of nitrogen at a temperature of 250° C. over the catalyst described above. After a short lead time of 15 minutes to establish constant operating conditions, the product mixture was collected over a period of one hour and then analyzed. 84.2% by weight of 2-chlorothiophene employed isomerized under these conditions to 3-chlorothiophene. Thiophene was found as a by-product (5.3%, based on the 2-chlorothiophene employed).

EXAMPLE 2

(Isomerization of 2-Bromothiophene)

15 ml/hour of a mixture of 2-bromothiophene and benzene in a ratio of 1:10 were passed together with 5 l/hour of nitrogen at a temperature of 210° C. over the catalyst described above. After a short lead time of 15 minutes to establish constant operating conditions, the product mixture was collected over a period of 4 hours by changing the receiver hourly, and was then analyzed. Table 1 shows the results thereby obtained.

TABLE 1

| | Isomerization of 2-bromothiophene | |
|---|---|---|
| Duration (hours) | Yield of 3-bromothiophene (%) | Yield of thiophene (%) |
| 1 | 66.6 | 26.3 |
| 2 | 76.6 | 13.3 |
| 3 | 85.4 | 2.4 |
| 4 | 86.5 | 1.3 |

After a short initial phase in which a relatively large amount of thiophene was formed, the catalyst showed very selective properties.

From the fifth hour onwards, 5 ml/hour of 2-bromothiophene (without added benzene) and 5 l/hour of nitrogen were passed over the catalyst at 210° C. for a further 2 hours. The yield of 3-bromothiophene was 82.6%. The yield of the by-product thiophene was 2.8%. Other by-products were formed only in amounts of less than 1%.

EXAMPLE 3

(Isomerization of 2-Bromothiophene on a Regenerated Catalyst)

The catalyst which had already been used for carrying out Example 2 was regenerated, after a total of 16 operating hours, with 20 l/hour of nitrogen and 5 l/hour of air for one hour, then with 20 l/hour of nitrogen and 10 l/hour of air for one hour, and subsequently with 10 l/hour of nitrogen and 10 l/hour of air for a further hour, in each case at 500° C..

5 ml/hour of 2-bromothiophene and 5 l/hour of nitrogen were then passed over the catalyst at 210° C. for two hours. The yield of 3-bromothiophene was 74.3% in the first hour and 79.8% in the second hour, and the yield of thiophene was 5.8% in the first hour and 3.5% in the second hour. This shows that the complete catalytic activity was restored by the regeneration.

We claim:

1. A process for isomerizing a mono-, di- or trihalogenated thiophene containing a halogen at an alpha position by moving the halogen to an adjacent beta position, which comprises bringing the mono-, di- or trihalogenated thiophene, or a mixture thereof, into contact with a zeolite catalyst of the pentasil, mordenite or faujasite type at a temperature between 150° and 550° C.

2. The process as claimed in claim 1, wherein an acid zeolite of the pentasil, mordenite or faujasite type is employed.

3. The process as claimed in claim 1, wherein an acid zeolite of the pentasil type is employed.

4. The process as claimed in claim 2, wherein the acid zeolite contains protons as cations.

5. The process as claimed in claim 1, wherein the reaction is carried out in the presence of benzene, an alkylbenzene or a halogenated benzene or a mixture of these.

6. The process as claimed in claim 1, wherein the reaction is carried out at a pressure of between 0.1 and 10 bar.

7. The process as claimed in claim 1, wherein the reaction is carried out in the presence of hydrogen, nitrogen, steam, argon or a mixture of these.

8. A process for the preparation of 3-chlorothiophene, which comprises bringing 2-chlorothiophene into contact with a zeolite catalyst of the pentasil, mordenite or faujasite type.

9. The process as claimed in claim 8, wherein an acid zeolite of the pentasil, mordenite or faujasite type is employed.

10. The process as claimed in claim 8, wherein an acid zeolite of the pentasil type is employed.

11. A process for the preparation of 3-bromothiophene, which comprises bringing 2-bromothiophene into contact with a zeolite catalyst of the pentasil, mordenite or faujasite type.

12. The process as claimed in claim 11, wherein an acid zeolite of the pentasil, mordenite or faujasite type is employed.

13. The process as claimed in claim 11, wherein an acid zeolite of the pentasil type is employed.

* * * * *